(12) United States Patent
Epshteyn et al.

(10) Patent No.: US 9,409,936 B2
(45) Date of Patent: Aug. 9, 2016

(54) PREPARATION OF GRAPHITIC C3N3P MATERIAL

(71) Applicants: Albert Epshteyn, College Park, MD (US); Brendan Yonke, Denver, CO (US); Timothy Strobel, Washington, DC (US); Huiyang Gou, Washington, DC (US)

(72) Inventors: Albert Epshteyn, College Park, MD (US); Brendan Yonke, Denver, CO (US); Timothy Strobel, Washington, DC (US); Huiyang Gou, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/819,563

(22) Filed: Aug. 6, 2015

(65) Prior Publication Data

US 2016/0176904 A1    Jun. 23, 2016

Related U.S. Application Data

(60) Provisional application No. 62/035,061, filed on Aug. 8, 2014.

(51) Int. Cl.
| | | |
|---|---|---|
| *C01B 21/097* | (2006.01) | |
| *C01B 21/082* | (2006.01) | |
| *C07F 9/6521* | (2006.01) | |
| *C07D 251/26* | (2006.01) | |

(52) U.S. Cl.
CPC ........... *C07F 9/65216* (2013.01); *C01B 21/082* (2013.01); *C01B 21/097* (2013.01); *C07D 251/26* (2013.01)

(58) Field of Classification Search
CPC . C07F 9/65216; C01B 21/097; C01B 21/082; C07D 251/26
USPC .................................. 544/193; 423/302, 364
See application file for complete search history.

(56) References Cited

U.S. PATENT DOCUMENTS

| | | | |
|---|---|---|---|
| 3,165,513 A | 1/1965 | D'Alelip | |
| 3,410,809 A | 11/1968 | Johns | |
| 7,708,971 B2 | 5/2010 | Lappalainen et al. | |

OTHER PUBLICATIONS

Zhang, Ligang et al., Materials Research Bulletin, vol. 48, 2013, pp. 3485-3491.
Zhang, Yuanjian et al., J. Am . Chem. Soc. vol. 132, 2010. pp. 6294-6295.
McMurran, Jeff et al., Chem. Mater. 1998. vol. 10, pp. 590-593.
Gou, HuiYang et al., J. Chem. Phys., May 18, 2015, vol. 142, 194503.
Chaloux, Brian L. et al. Chem. Mater. Jun. 11, 2015, vol. 27, pp. 4507-4510.
International Search Report and Opinion in PCT/2015/050231.
McMurran, J.; Kouvetakis, J.; Nesting, D. C.; Hubbard, J. L. Chem. Mater. 1998, 10, 590.
Kroke and Schwarz, Coordination Chemistry Reviews 248 (2004) 493-532.
Lin and Wang, Angew. Chem. Int. Ed. 2013, 52, 1735-1738.
Hou et al., Angew. Chem. Int. Ed. 2013, 52, 3621-3625.
Algara-Siller et al., Angew. Chem. Int. Ed 2014, 53, 7450.

*Primary Examiner* — Venkataraman Balasubramanian
(74) *Attorney, Agent, or Firm* — US Naval Research Laboratory; Roy Roberts

(57) ABSTRACT

A new graphitic material has the empirical formula $C_3N_3P$ and comprises triazine rings bound together by phosphorus atoms, and/or other 5- or 6-membered rings with various carbon, nitrogen, and phosphorous connectivity. The material is made by polymerizing $P(CN)_3$, for example by using a temperature of at least 220° C. and an elevated pressure, optionally as high as 1500° C. and 12 GPa.

12 Claims, 11 Drawing Sheets

PREPARATION OF GRAPHITIC C3N3P MATERIAL

CROSS-REFERENCE TO RELATED APPLICATIONS

This application claims the benefit of U.S. Provisional Application 62/035,061 filed on Aug. 8, 2014, the entirety of which is incorporated herein by reference.

BACKGROUND

Graphene has been suggested as a promising candidate material for electronics development. Most notably, graphene has the desirable combination of high charge-carrier mobility coupled with high current stability, temperature stability, and thermal conductivity. However, the (semi-)metallic character of graphene and the absence of an electronic bandgap have so far impeded the development of a graphene-based switch. Strategies to open up a graphene bandgap involve single- or multi-step modifications by physical and chemical means. Alternative, simpler routes to silicon-free electronic switches are based on known inherent semiconductors. One type of such materials are a class of triazine- (and possibly heptazine-) based graphitic carbon nitrides. A need exists for such materials and the methods to make them.

BRIEF SUMMARY

The invention relates to a new carbon-based extended solid material, namely a graphitic material with the empirical formula $C_3N_3P$. In can be made from $P(CN)_3$ as a molecular building block for cyano-trimerization.

In one embodiment, a method of making $C_3N_3P$ includes polymerizing $P(CN)_3$ to obtain a bulk polymer having the empirical formula $C_3N_3P$.

In another embodiment, a polymer has the empirical formula $C_3N_3P$ and comprises triazine rings bound together by phosphorus atoms, and/or other 5- or 6-membered rings with various carbon, nitrogen, and phosphorous connectivity.

DETAILED DESCRIPTION

Definitions

Figure 1:
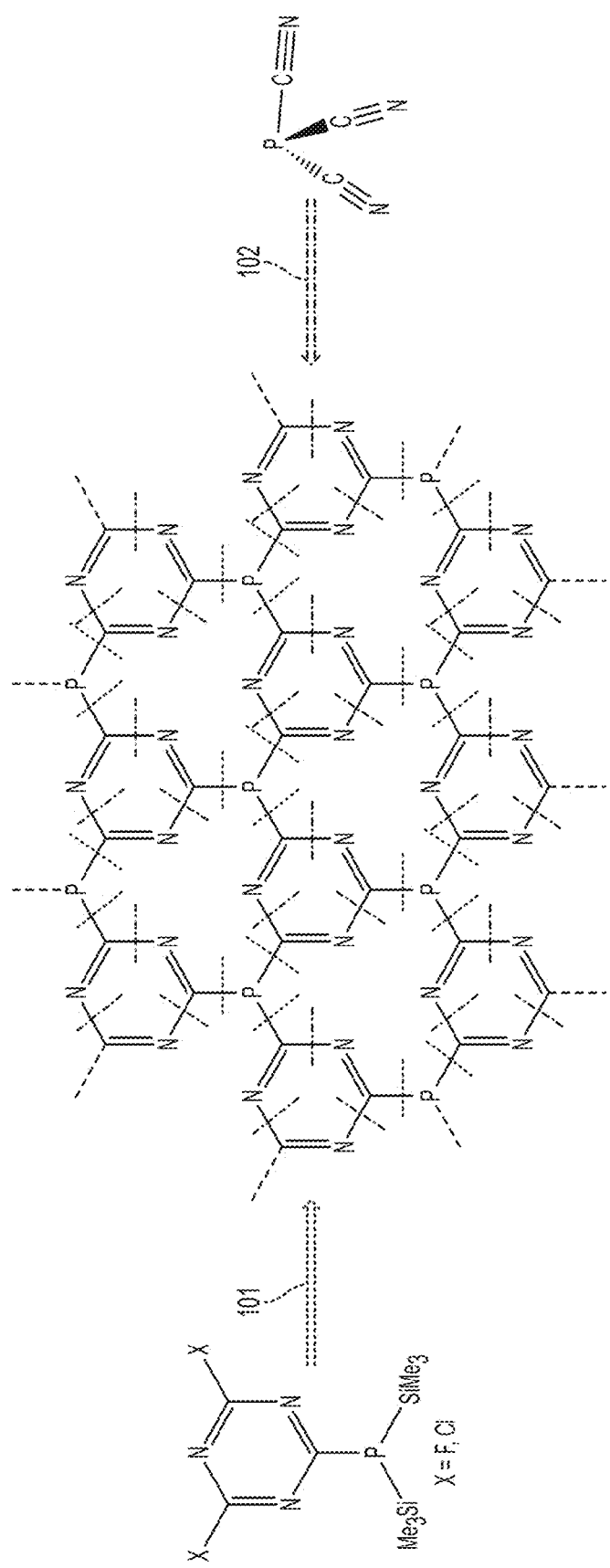
FIG. 1 shows a synthetic approach for obtaining polymeric $C_3N_3P$ according to the present invention compared to a technique proposed by McMurran et al., Chem. Mater. 1998, 10, 590-593.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "graphitic" refers to a material having a layered structure similar to graphite.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

A new graphitic material having the empirical formula $C_3N_3P$ is described herein, along with methods of making it. Aspects of the invention are described in J. Chem. Phys. 142, 194503 (2015), which is incorporated herein by reference.

In this case, cyano-trimerization (e.g., by thermal polymerization) of tricyanophosphine (also known as phosphorus(III) cyanide, $P(CN)_3$, or phosphorus tricyanide) produces a material consisting essentially of 5- or 6-membered rings with various carbon, nitrogen, and phosphorous connectivity, such as triazine aromatic rings bound together by phosphorus atoms. These materials have the empirical formula $C_3N_3P$.

Spectroscopic data confirms that the nitrile groups in the starting material disappear and new graphitic-type modes appear in the IR and Raman spectra. When the polymerization occurred under certain conditions, specifically, 12 GPa and 1500° C., evidence from high-resolution transmission electron microscopy (HR-TEM) showed that the product appears to be graphitic in form, while still retaining its 3C:3N:P elemental ratio (empirical formula). Furthermore, the material visually appears to be lustrous, metallic-like and preliminary bulk conductivity measurements suggest that it may be a semiconductor, which is in line with a report on $C_3N_4$ analog material in Algara-Siller et al., *Angew. Chem. Int. Edit* 2014, 53, 7450.

Previous attempts to produce $C_3N_3P$ graphitic extended solids were relatively unsuccessful, as the constituent building blocks used produced a gaseous halosilane byproduct that likely prevented the production of a crystalline product, with a report of production of an amorphous powder. McMurran, J.; Kouvetakis, J.; Nesting, D.C. *Chem. Mater.* 1998, 10, 590-593.

To reduce or eliminate the presence of byproducts, the present approach uses $P(CN)_3$, a stable, known compound, as the molecular building block. This starting material has the marked advantages of being easily made from $PCl_3$ and AgCN, being easily purified by sublimation, and being a monomeric species, in contrast to $C_3N_4$, which is likely due to a greater—CN trimerization barrier due to the higher barrier to inversion through the P center. Described below are the results of polymerizing $P(CN)_3$ at various conditions: at 220° C. and low pressures in a tube sealed under vacuum, at moderate pressures in a die heated to 400° C. and compressed to 20K psi in a Carver press, and at 12 GPa and 1500° C. in a multi-anvil press.

FIG. 1 shows a synthetic approach for obtaining polymeric $C_3N_3P$ according to the present invention (102) compared to the above-mentioned technique (101) proposed by McMurran et al., Chem. Mater. 1998, 10, 590-593 which undesirably forms a halosilane byproduct.

An attempt at polymerization of white crystalline $P(CN)_3$ powder in a sealed tube under vacuum and at 220° C. resulted in the formation of a dark (black) material similar to that reported by McMurran et al.

Figure 2:
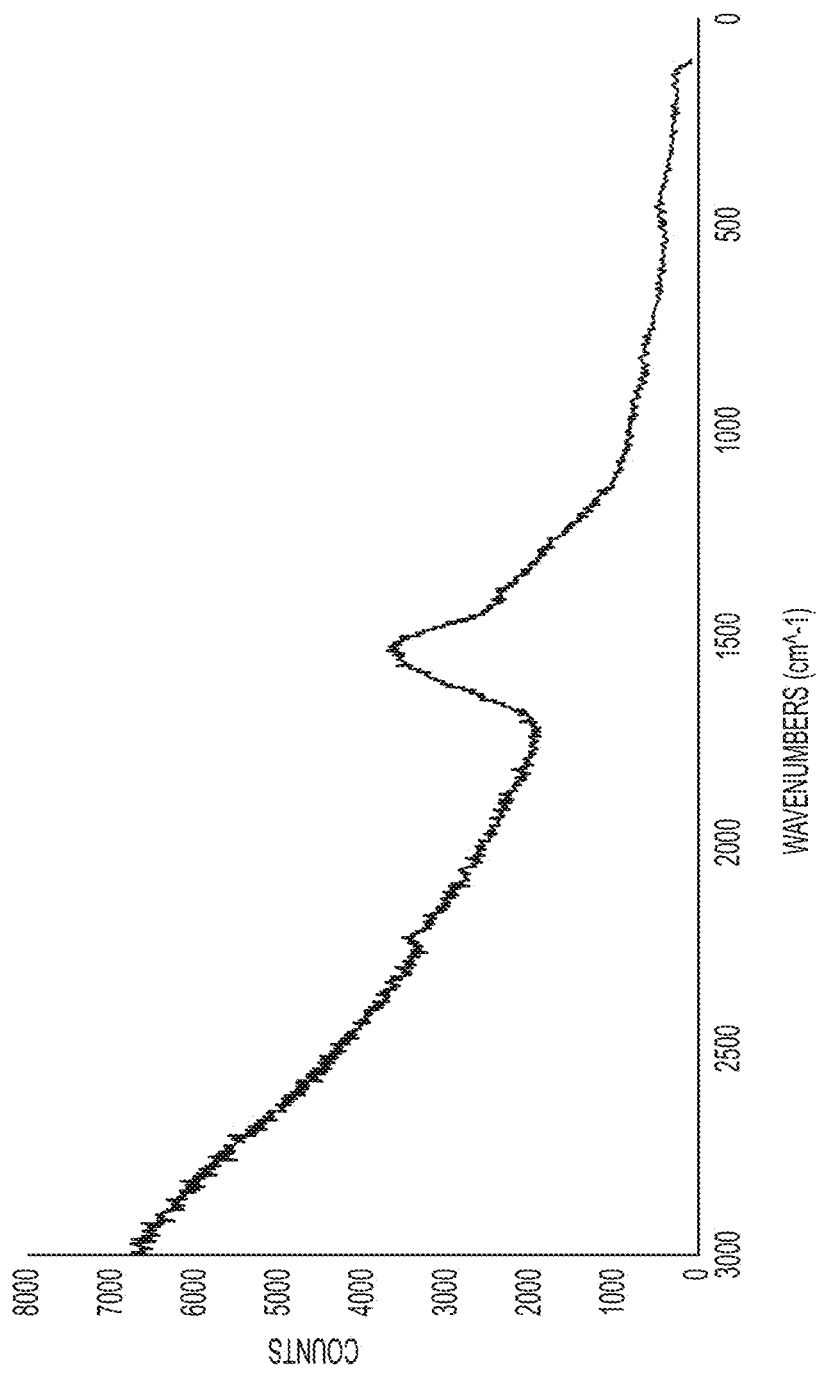
FIG. 2 is a Raman spectrum of $P(CN)_3$ powder polymerized in a sealed tube under vacuum at 220° C.

The transformation was confirmed with Raman spectroscopy (FIG. 2). Based on the Raman spectrum, it appears that the nitrile stretches of $P(CN)_3$ have almost completely vanished, with only a tiny peak still appearing 2300 wavenumbers. The majority of the material has been transformed, with new broad graphitic stretches appearing near 1500 $cm^{-1}$. Based on this spectrum, the graphitic material is not very well defined (inhomogeneous) with the D and L bands overlapping to make a single broad peak with a shoulder.

Figure 3:
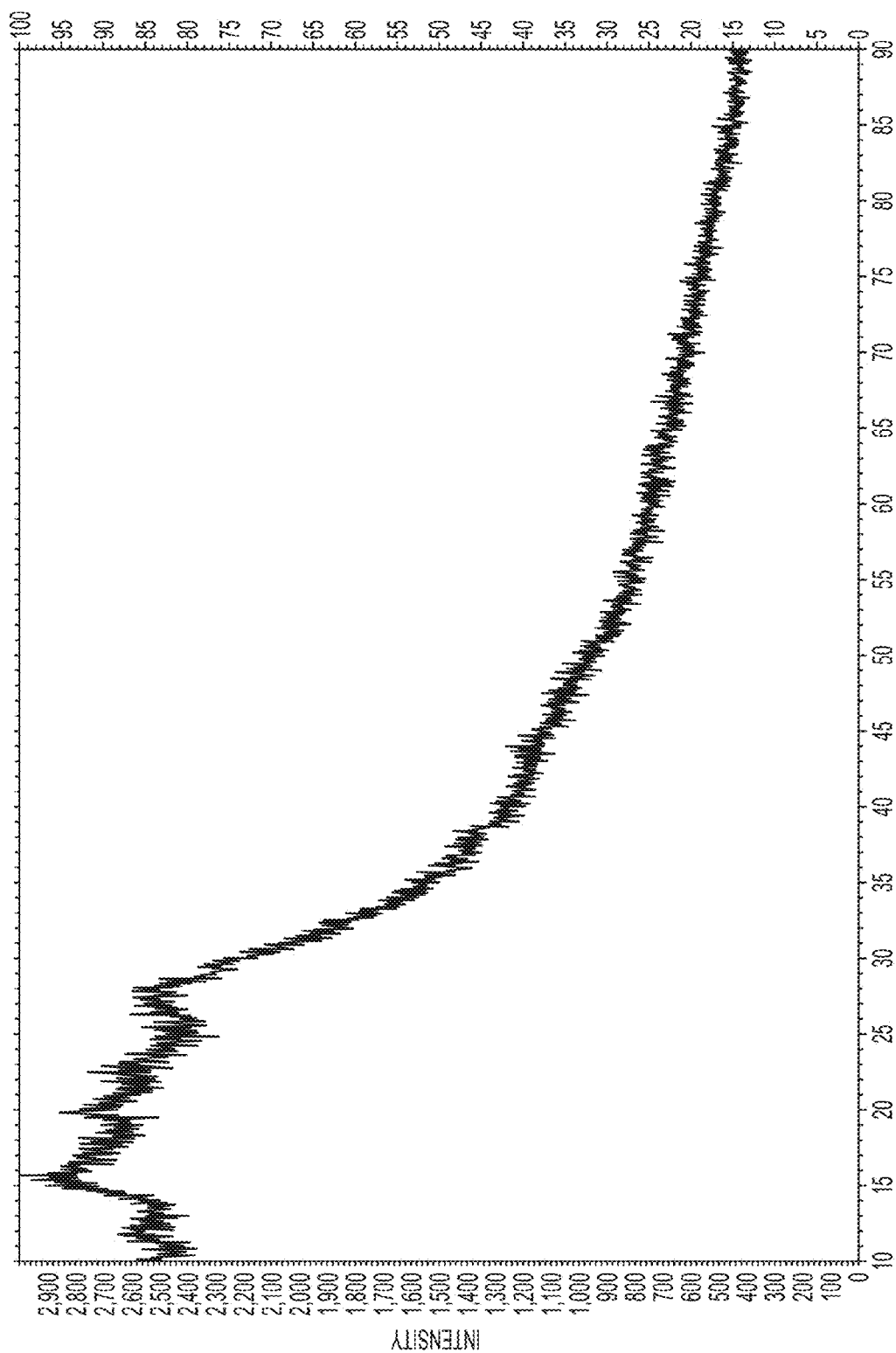
FIG. 3 shows results of powder x-ray diffraction (PXRD) analysis of the same sample as in FIG. 2.

Powder x-ray diffraction (PXRD) analysis of the non-air exposed sample showed some broad low angle peaks suggestive of a graphitic microstructure (FIG. 3).

Figure 4:
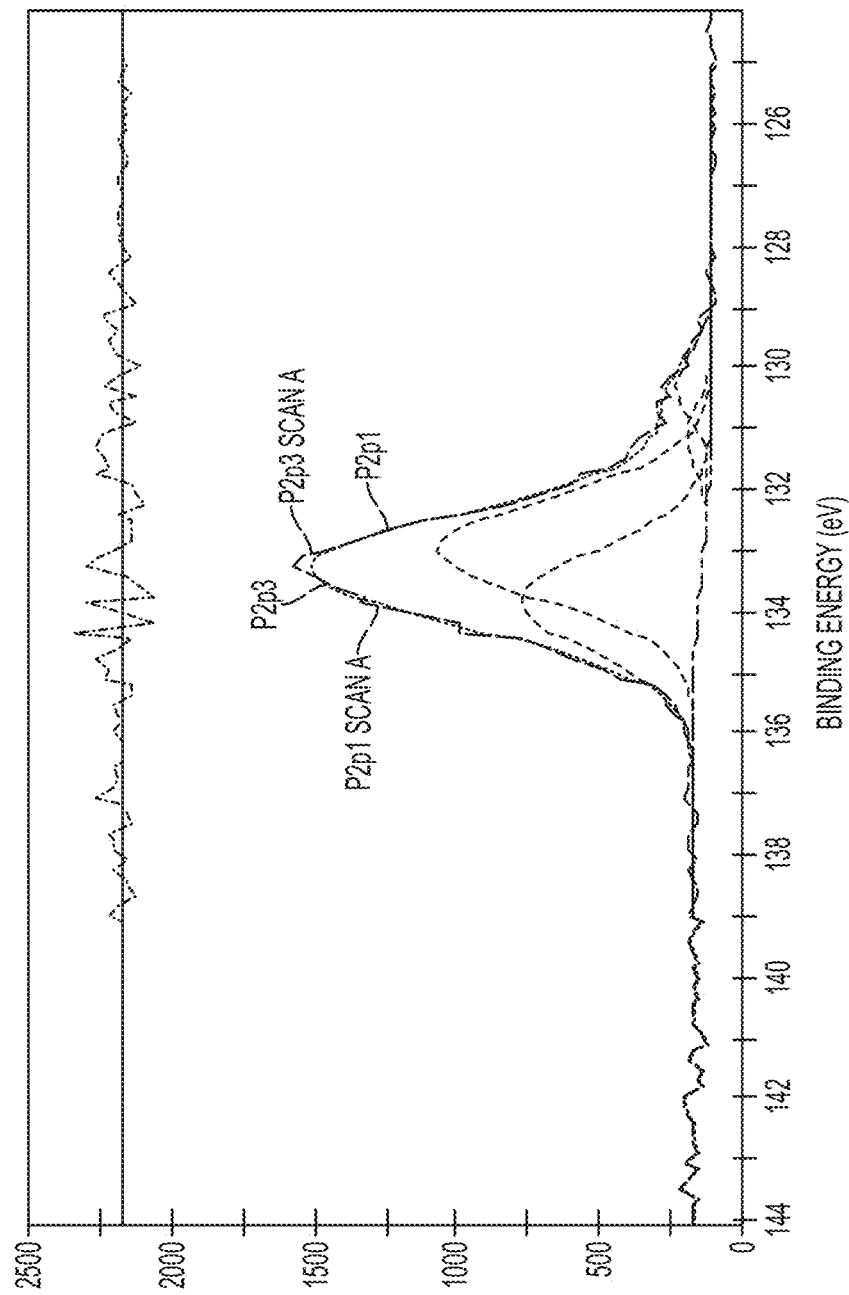
FIG. 4 is an x-ray photoelectron spectroscopy (XPS) core level spectrum of the P in the black polymer C3N3P powder confirming that nearly all of the P is oxidized (133 kV BE) as opposed to the small reduced P shoulder appearing at 131 kV.

X-ray photoelectron spectroscopy (XPS) on the same material, now exposed to air (FIG. 4), showed that nearly all of the phosphorus in the sample is the V and not the III oxidation state.

Figure 5:
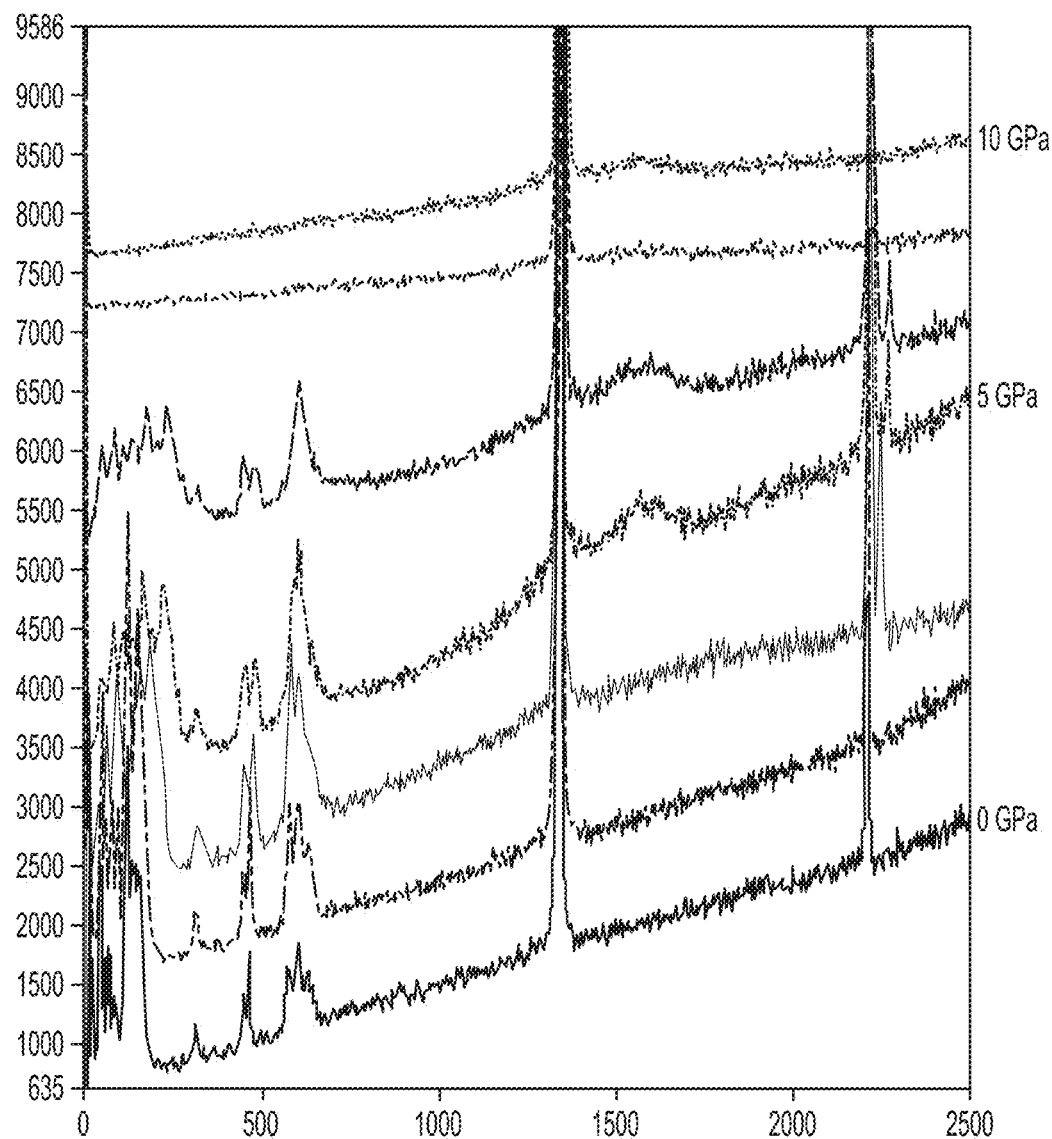
FIG. 5 shows an XPS core level spectrum of the P in the black polymer $C_3N_3P$ powder confirming that nearly all of the P is oxidized (133 kV BE) as opposed to the small reduced P shoulder appearing at 131 kV.

Attempts to produce a graphitic material using a conventional hydraulic laboratory press and elevated temperatures resulted in partial polymerization taking place at pressures as low as 15000 psi and temperatures as low as 400° C. Cold compression experiments in a diamond anvil cell (DAC) were then conducted, showing that under only the action of pressure the material begins to polymerize around 5 GPa at ambient room temperature (FIG. 5).

Figure 6:
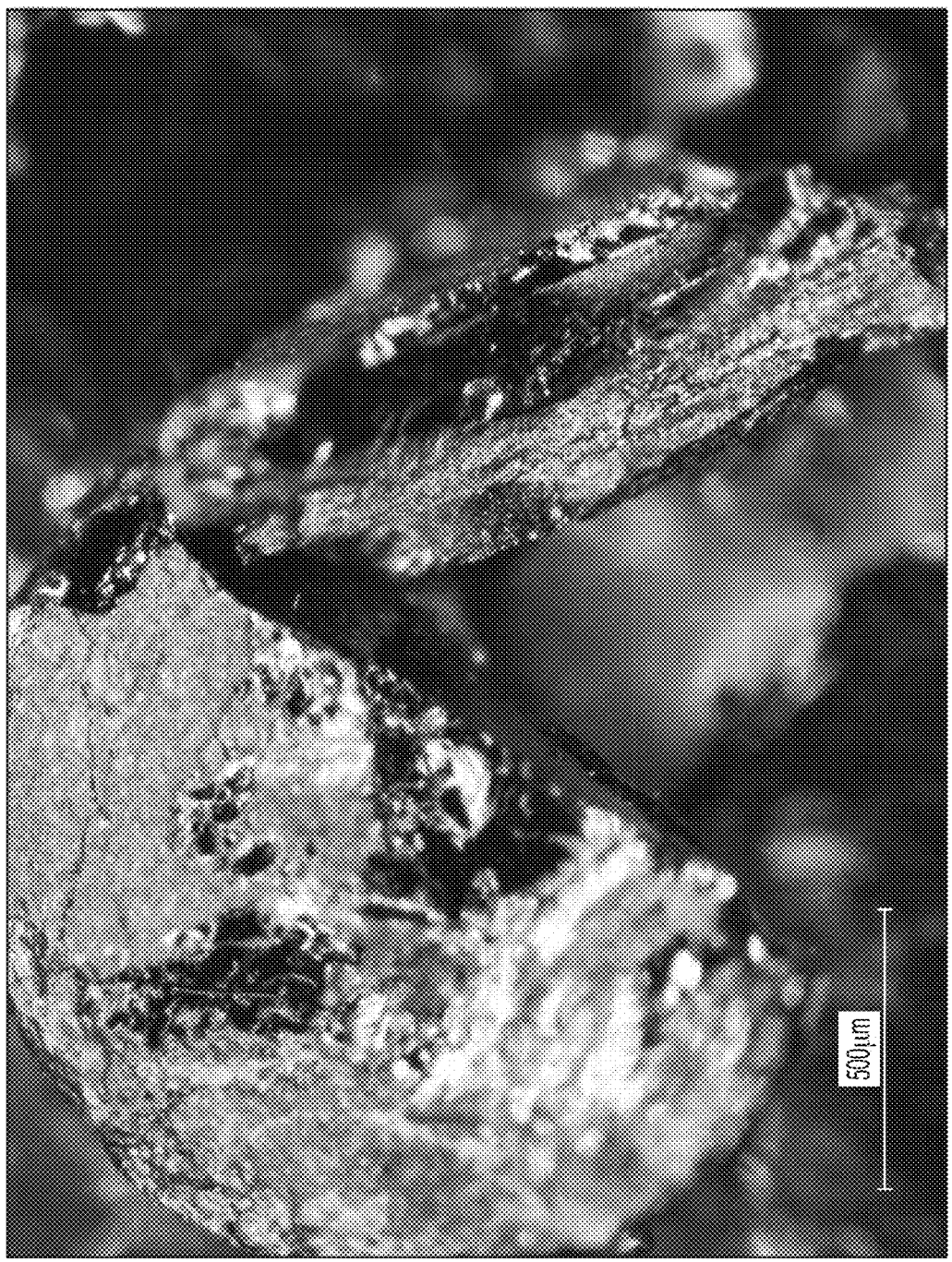
FIG. 6 is an optical micrograph of cleaved monolithic $C_3N_3P$ sample obtained at 12 GPa and 1500° C., exposing the interior of the sample.
Figure 7B:
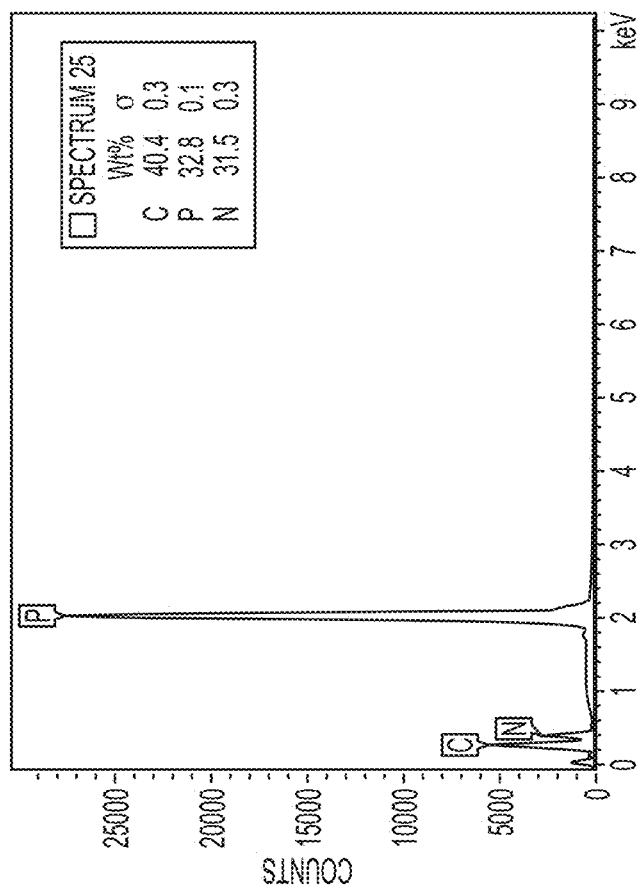
FIG. 7B is an energy-dispersive X-ray spectroscopy (EDS) spectrum of the monolith surface confirming the C, N, and P are present in the desired ratio.
Figure 7A:
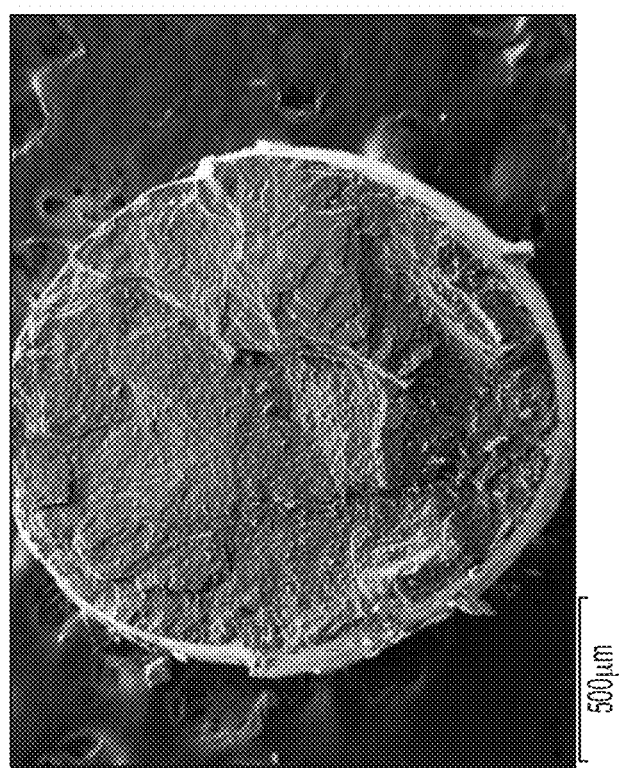
FIG. 7A a scanning electron microscopy (SEM) micrograph of the $C_3N_3P$ monolith.

Additional experiment used a larger $P(CN)_3$ sample in a multi-anvil cell at 12 GPa, a pressure selected based on the cold compression DAC experiments as the pressure where the reaction appeared to be completed. The temperature of 1500° C. was used, corresponding to the upper temperature limit for the cell heaters being used in the experiment. The resulting sample appeared to be monolithic as can be seen in the optical micrograph in FIG. 6. The material clearly appears to be a lustrous metallic monolith. Electron microscopy data by SEM and the EDS spectrum of the monolith are suggestive of a layered "flaky" structure with the EDS spectrum confirming that the C—N—P ratio in the product material has remained intact (FIGS. 7A and 7B).

Figure 8:
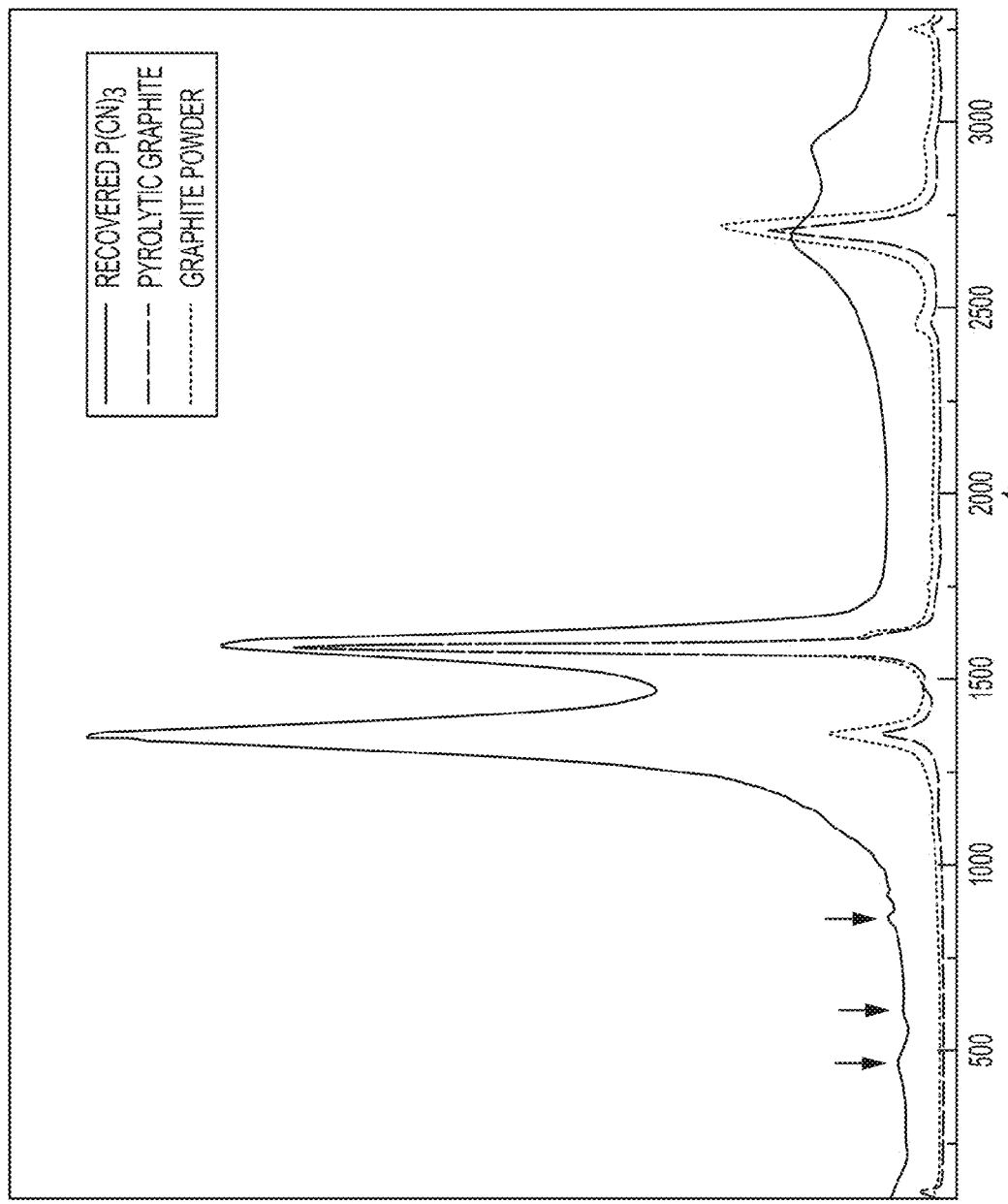
FIG. 8 is a Raman spectrum of the $P(CN)_3$ recovered from 12 GPa and 1500 C overlayed with spectra of pyrolytic graphite and graphite powder.
Figure 9A:
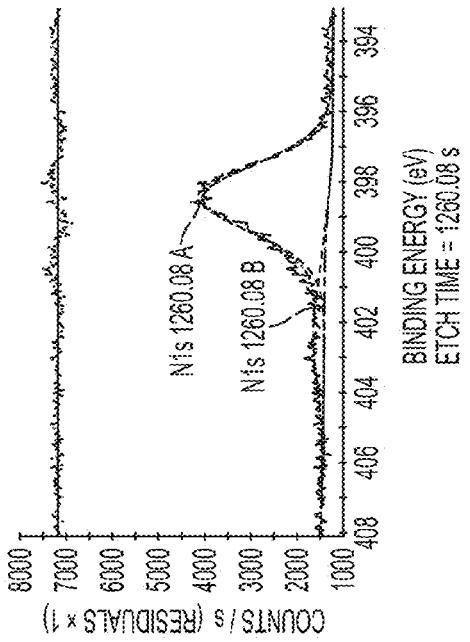
FIGS. 9A-9D show XPS core level spectra of C 1s (FIG. 9A), N 1s (FIG. 9B), P 2p (FIG. 9C), and O 1s (FIG. 9D) of an area of a $C_3N_3P$ monolith that has been ion milled down to about 0.3 μm from the surface.
Figure 9B:
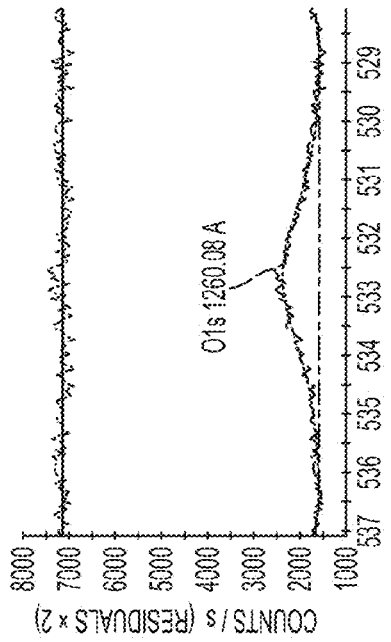
Figure 9C:
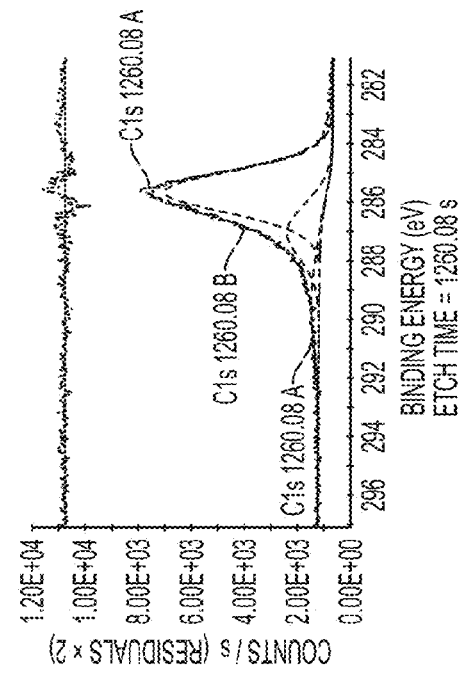
Figure 9D:
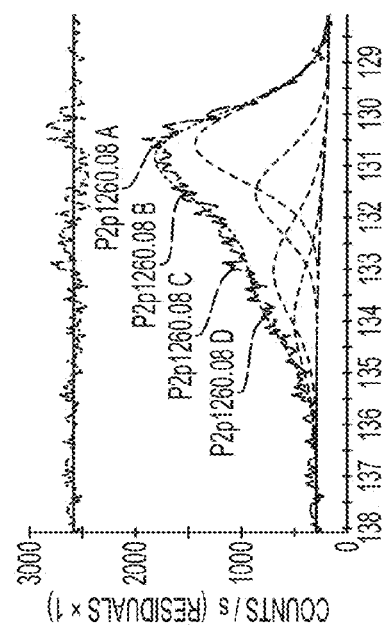

Raman spectroscopy of the monolith (FIG. 8) shows well-defined D and L graphitic bands that are suggestive of a better defined graphitic structure compared to material made under vacuum, and the Raman bands are similar to those of other known graphitic materials. XPS of the a monolithic sample after ion milling down to a depth of about 0.3 μm revealed that this sample is likely much more dense than the samples produced in the original polymerization attempts at low pressure (FIG. 9). The XPS spectra at the surface were more like the low density black powder obtained at low pressures. However, after ion milling, the O signal diminished even a few 10s of nanometers into the sample, and persisted at various depths. The spectra obtained at this level show that a significant portion of the sample contains P(III), but the P(V) signal at 133 kV still persists. It was not possible to ion mill it away. This is confirmed by the persisting O signal as well, and suggestive of the material being porous (allowing oxygen to infiltrate), and not yet fully dense. The P atoms exposed due to the remaining porosity are likely the ones that are oxidized after air exposure.

Figure 10A:
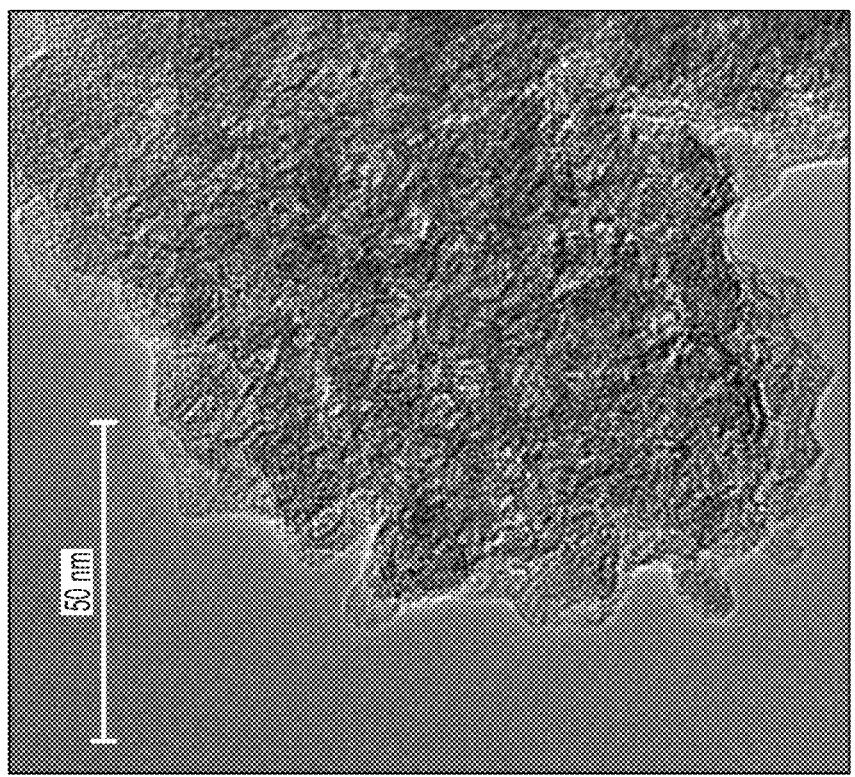
FIG. 10A is a TEM micrograph of the graphitic monolith sample revealing a porous structure.
Figure 10B:
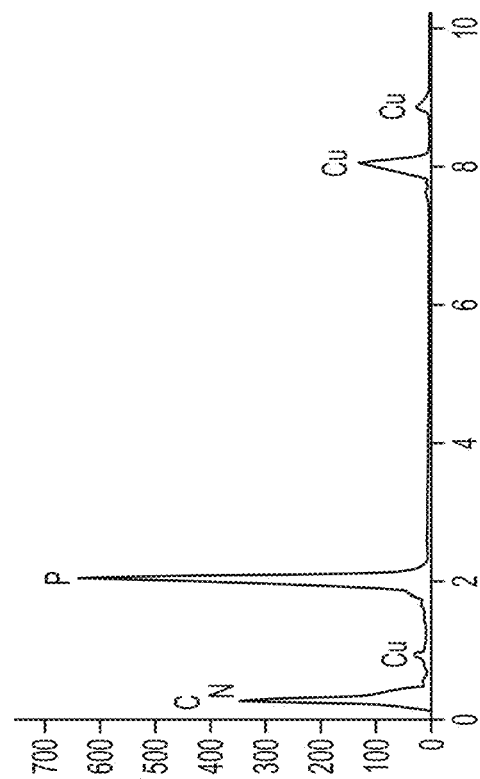
FIG. 10B is an EDS spectrum confirming the presence of only C, N and P (Cu is from the TEM grid).
Figure 11A:
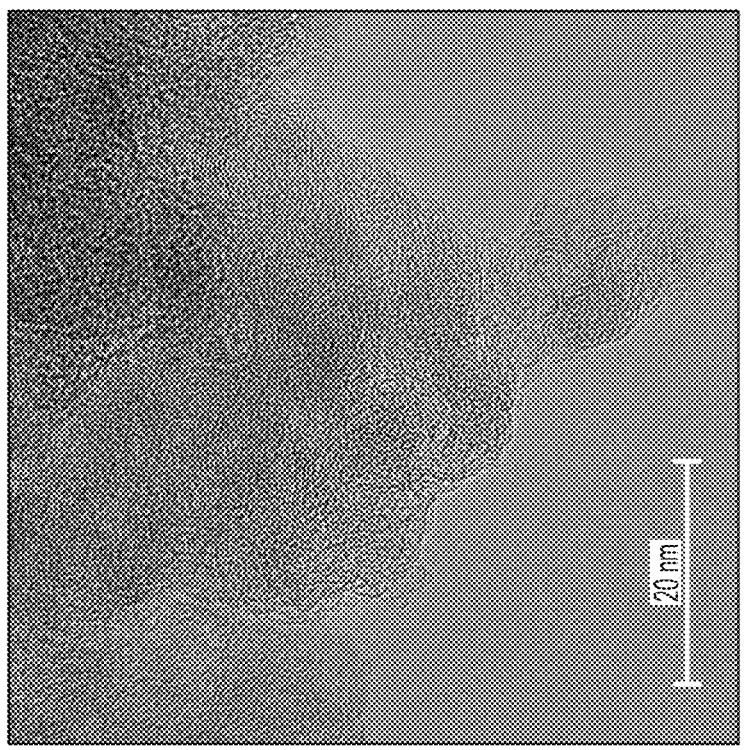
FIGS. 11A and 11B shows graphitic microstructure of the material as revealed by HR-TEM. The inset in FIG. 11A is a fast Fourier transform (FFT) diffractogram.
Figure 11B:
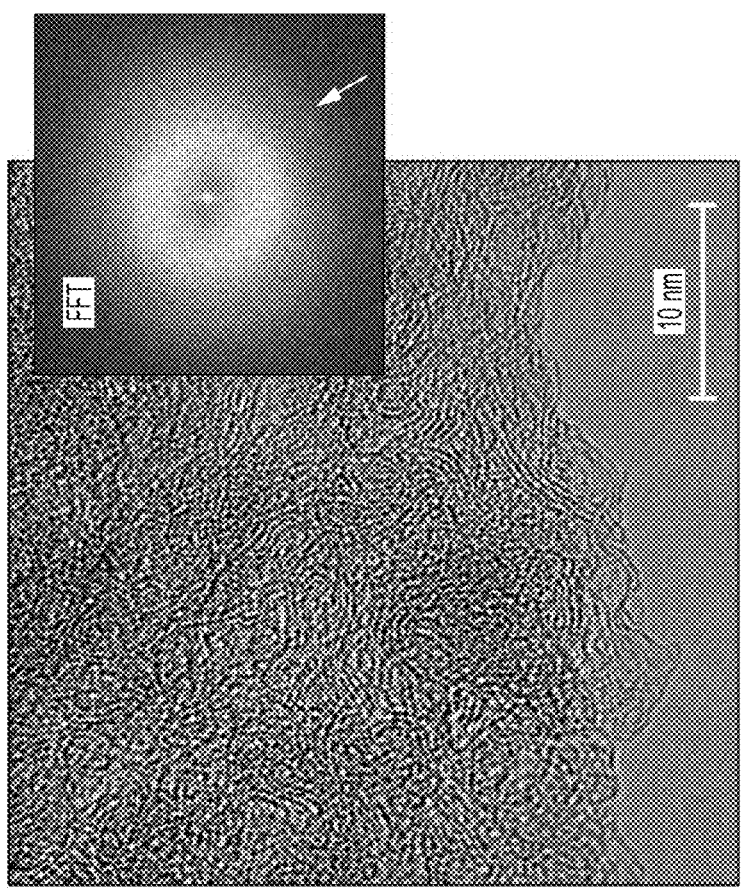

The indication that the material is not yet fully dense was further confirmed by HR-TEM. A portion of the monolith was ground with a mortar and pestle, dispersed in ethanol, and a droplet deposited on a TEM grid. FIG. 10A shows a lower resolution micrograph of the graphitic structure that reveals a highly porous structure. More importantly, closer examination by HR-TEM of the sample reveals a graphitic structure reminiscent of graphitic carbon materials, as can be seen in FIG. 11. In particular, FIG. 11A shows what appear to be edges of nanoscale sheets, curled as an artifact of sample preparation.

The above evidence indicates the synthesis of a $C_3N_3P$ graphitic material. The $C_3N_3P$ material is technologically important for its potential of having a lower energy barrier for a transition from a graphitic into a cubic structure (see Ding, F.; Feng, Y. P. Comput. Mater. Sci. 2004, 30, 364). Furthermore, the graphitic material itself is a semiconductor and should have interesting opto-electronic properties (see Zhang, Y. J.; Mori, T.; Ye, J. H.; Antonietti, M. *J. Am. Chem. Soc.* 2010, 132, 6294). The material is expected to have potential for use in graphene-based electronics, as well as photo- and electro-catalysis.

It is expected that a $C_3N_3P$ graphitic material might be obtainable from polymerization of phosphorous tricyanide at temperatures and pressures other than those used in these experiments. For example, a reaction might be conducted at a temperature between about 400° C. and about 2500° C. and at a pressure from about 100 MPa to about 460 GPa.

Concluding Remarks

All documents mentioned herein (including the accompanying material filed herewith) are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

ADDITIONAL REFERENCES

Liu, A. Y.; Cohen, M. L. *Science,* 1989, 245, 841-842.
Teter, D. M.; Hemley, R. J. *Science,* 1996, 271, 53-55

What is claimed is:

1. A method of making $C_3N_3P$, the method comprising:
polymerizing $P(CN)_3$ to obtain a bulk polymer having the empirical formula $C_3N_3P$.

2. The method of claim 1, wherein the polymerizing comprises subjecting said $P(CN)_3$ to a temperature of 220° C. or greater and a pressure of two atmospheres or greater.

3. The method of claim 2, wherein said temperature is at least 400° C.

4. The method of claim 2, wherein said pressure is at least 20,000 pounds per square inch.

5. The method of claim 2, wherein said pressure is at least 10 GPa.

6. The method of claim 1, wherein said bulk polymer comprises triazine rings bound together by phosphorus atoms.

7. A material comprising a polymer having the empirical formula $C_3N_3P$ and comprising 5- or 6-membered rings with various carbon, nitrogen, and phosphorous connectivity.

8. The material of claim 7, having a graphitic form.

9. The material of claim 7, having a nanocrystalline form.

10. The material of claim 7, consisting primarily of triazine rings bound together by phosphorus atoms.

11. A material comprising a polymer having the empirical formula $C_3N_3P$ and comprising triazine rings bound together by phosphorus atoms, wherein the material consists primarily of nanoscale sheets of the polymer.

12. The material of claim 11, further consisting primarily of said triazine rings bound together by phosphorus atoms.

* * * * *